United States Patent [19]

Segal

[11] Patent Number: 4,840,564
[45] Date of Patent: Jun. 20, 1989

[54] DENTAL MEASURING APPARATUS

[76] Inventor: Alan J. Segal, 13 Park Avenue, Hale, Cheshire, WA15 9DL, United Kingdom

[21] Appl. No.: 120,844

[22] Filed: Nov. 16, 1987

[30] Foreign Application Priority Data

Nov. 20, 1986 [GB] United Kingdom ............... 8627776

[51] Int. Cl.⁴ ............................................ A61C 19/04
[52] U.S. Cl. ...................................... 433/72; 33/513
[58] Field of Search ....................... 433/72, 75, 76, 56, 433/57; 33/513, 514, 511, 1 M, 551

[56] References Cited

U.S. PATENT DOCUMENTS 1,296,643  3/1919  Fish ....................................... 33/513
3,374,548  3/1968  Romney ................................. 33/511
4,370,130  1/1983  Berger ................................... 433/32
4,573,917  3/1986  Erickson ................................ 433/72

Primary Examiner—Robert Peshock
Attorney, Agent, or Firm—Pearson & Pearson

[57] ABSTRACT

A dental measuring apparatus is provided for accurately measuring dentures, models, bite blocks and the like, and comprises a table, a support and a probe. On the table is marked a datum point and a scale indicating distances from the datum point. The probe is movable relative to the support axially of itself towards and away from the datum point. A scale is marked on the support to indicate the height of the probe above the datum point.

10 Claims, 2 Drawing Sheets

DENTAL MEASURING APPARATUS

This invention relates to dental measuring apparatus, and in particular to apparatus for use in prosthetics.

Prosthetics is that branch of dentistry concerned with the production of dentures to replace missing teeth. The dentures may be partial or full, and the process of making such dentures is relatively long and involved. If great care is not taken by the dental technician in the making of the dentures, the fit and/or bite registration will not be correct and the patient can suffer discomfort and/or disfigurement. To correct these faults takes further time and effort on the part of the technician and dentist and can be disconcerting to the patient.

The process of making dentures involves firstly the taking of impressions in the patient's mouth by the dentist using an impression material (E.g impression paste, plaster of Paris, alginate or the like) in impression trays. These impressions are used by the dental technician in the laboratory to cast models of the patient's jaws, for example in plaster of Paris. The technician also produces bite blocks, each comprising a wax material rim on a baseplate in the position the teeth would be thereon, for a bite or occlusial registration which is performed in the surgery by the dentist. When the bite blocks appear to be satisfactory they are returned to the laboratory and are placed with the models by the technician in an articulator, which should locate the models and bite blocks in their correct relative disposition as obtained at the bite stage. The bite rims are removed from their base plates and the false teeth are set up in wax in their place. These are then sent back to the surgery for fitting to the patient by the dentist during what is known as the "try-in" stage. Adjustments may have to be made requiring further work in the laboratory by the technician and subsequent "try-in" operations. When these "waxed-up" dentures are considered satisfactory they are returned to the laboratory to be made into finished dentures, involving "flasking, to replace the wax by acrylic material, packing and polishing" stages, which are then finally fitted to the patient by the dentist in the surgery.

Many of the above operations are of the "trial and error" variety and the amount of work and time involved depends to a very large extent on the skill and experience of both dentist and technician and the quality of communication between them.

It is an object of the present invention to provide a dental measuring apparatus, the use of which will avoid or reduce to a considerable extent the "trial and error" nature of denture manufacture and enable quantitative information to pass between the dentist and the technician to assist in the accurate production of the dentures.

The invention provides a dental measuring apparatus comprising a table having a datum point located thereon, support means adjacent said table, a probe mounted on said support means and movable axially relative to said table, said probe axis being aligned with said datum point, first indicating means adapted to indicate the height of said probe above said datum point, and second indicating means on said table adapted to indicate distances on said table from said datum point.

Said probe may comprise an elongate needle, and may be resiliently biassed away from said table. Locking means may be provided whereby said probe may be secured in any position of adjustment relative to said table.

Embodiments of apparatus in accordance with the invention will now be described with reference to the accompanying drawings in which.

Figure 1:
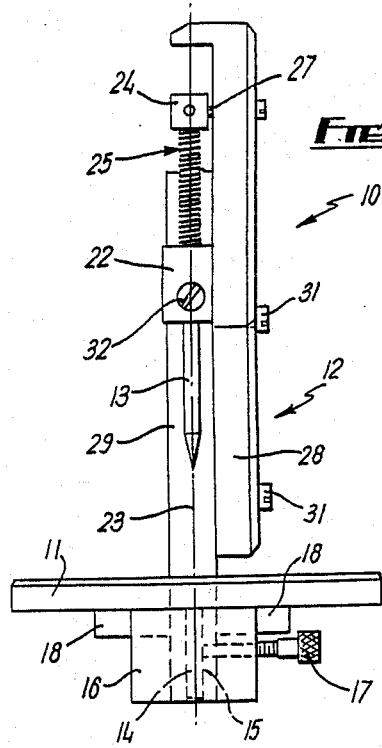
FIG. 1 is a front elevation of one embodiment.
Figure 2:
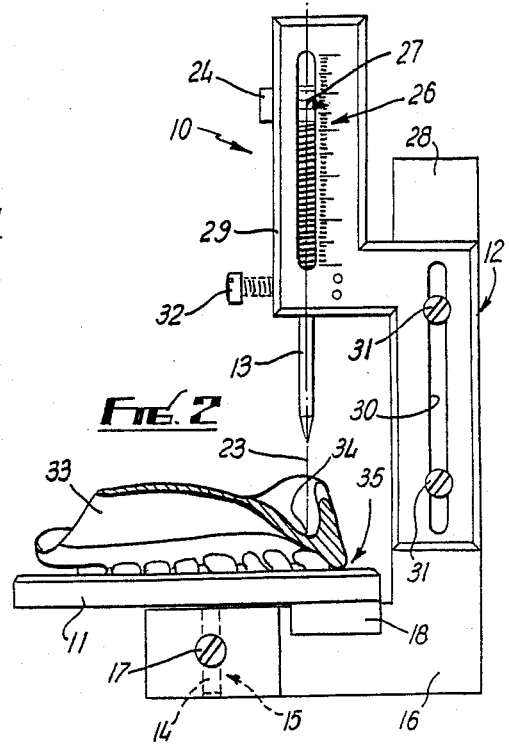
FIG. 2 is a side elevation of the embodiment of FIG. 1.
Figure 3:
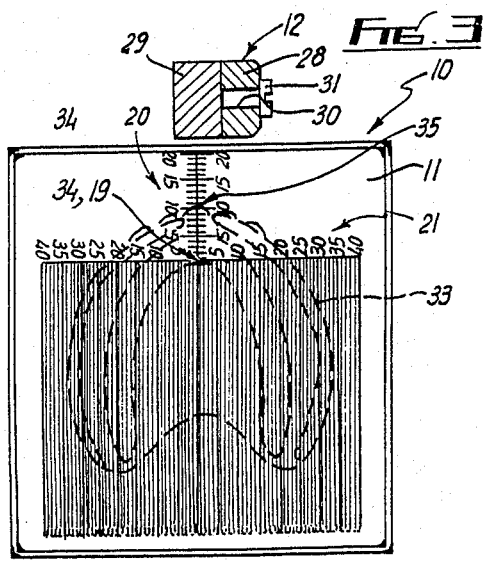
FIG. 3 is a plan view of the embodiment of FIG. 1.

Referring now to FIGS. 1 to 3 there is shown a dental measuring apparatus 10 comprising a table 11, a pillar 12 and a probe 13. The table 11 and pillar 12 are conveniently made of a plastics material although any suitable material, such as metal, may be used. The table 11 has a depending post 14 which is received in a bore 15 in a base part 16 of the pillar 12 and which is releasably secured therein by a retaining screw 17. The table 11 also has two depending locating bosses 18 which contact opposed sides of the base part 16 to locate the table 11 correctly relative to the pillar 12. On the upper surface of the table 11 is marked a datum point 19 and a first scale 20 in any appropriate units is marked on the upper surface of the table 11 to indicate distances on the table 11 from the datum point 19. A second scale 21 may also be marked on the upper surface of the table 11 to indicate distances on the table 11 from the datum point 19 in a direction perpendicular to the scale 20.

The pillar 12 comprises a bush part 22 in which is slidingly received a probe 13. The probe 13 can move axially of itself and is located such that the datum point 19 lines on the probe axis 23. A stop 24 is provided on the upper end of the probe 13 and a compression spring 25 is disposed around the probe 13 between the bush part 22 and the stop 24. By this means the probe 13 is resiliently biassed in an upwards direction away from the datum point 19 on the table 11. A scale 26 is marked on the pillar 12 and a pointer 27 is affixed to the stop 24 so as to move with the probe 13 and adjacent the scale 26. The pillar 12 is in two, relatively adjustable, parts 28,29, part 29 having an elongate slot 30 therein through which two screws 31 pass to be received in threaded bores (not shown) in the pillar part 28. A probe clamping screw 32 is provided in bush part 22 so that the probe 13 can be clamped in any position of adjustment. By slackening the screws 31,32 and suitable positioning of the pillar parts 28,29 it can be arranged that the pointer 27 is aligned with the zero on the scale 26 with the probe 13 in a downward position of adjustment relative to the pillar 12 and in contact with the table 11 at the datum point 19. The screws 31 are then tightened and the probe 13 allowed to move under the force of the spring 25 to its most upward position relative to the pillar 12.

The apparatus 10 is used in the following manner. An object to be measured, for example a denture 33, is placed on the table 11, as shown in FIG. 2 and in dashed lines in FIG. 3. The probe is then lowered so as to contact the denture 33 at the upper incisive papillae position 34 of an upper denture 33 or corresponding lower mid-line or centre spot position on the crest of the central ridge of a lower denture 33. These positions 34 provide a particularly suitable datum location which can readily be identified on the denture 33 or in the mouth of the patient so that measurements made relative to such datum point on the impressions, if reproduced faithfully in the dentures will ensure a satisfactory positioning of the teeth in the patient's mouth. The probe 13 ca be secured in this denture contacting position by means of screw 32 if desired whilst the requisite readings are taken. The reading of the pointer 27 on the scale 26 represents the vertical distance of the incisal tip 35 of the front teeth (centrals or incisors) from the incisive papillae or lower centre spot datum 34. The reading of the incisal tip 35 of the front teeth on scale 20 on the table 11 represents the horizontal distance of the incisal tip 35 from the datum 34. By this means a quantitative assessment of the denture 33 can be made. In addition if required the distance of the two sides of the denture 33 from the datum 34 can be measured using the scale 21 on the table 11.

Figure 4:
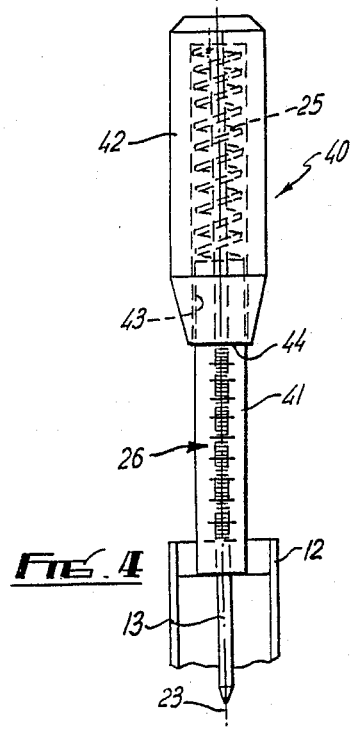
FIG. 4 is a front elevation of a second embodiment.

Referring now to FIG. 4 there is shown an alternative embodiment of dental measuring apparatus 40. The apparatus 40 comprises a table 11 (not shown), pillar 12 and probe 13 corresponding with those part of the apparatus 10 previously described. In this case however mounted on the pillar 12 is a barrel 41 having an axial bore in which the probe 13 is slidingly received. A scale 26 is marked on the barrel 41. The upper end of the probe 13 is secured in a cap 42 which has an axial bore 43 which will slidingly receive the barrel 41. A compression spring 25 is located in the bore 43, one end of the spring 25 being in contact with the end of the cap 42 and the other end of the spring 25 being in contact with the upper end of the barrel 41 so as to bias the cap 42 and the probe 13 upwardly. The lower edge 44 of the cap 42 moves over the scale 26 in order that readings may be taken. Operation of the apparatus 40 is the same as that of the apparatus 10.

Figure 5:
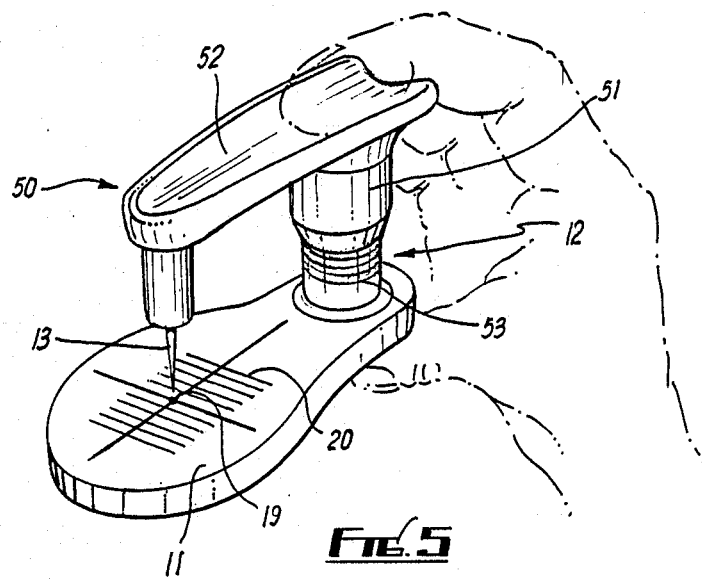
FIGS. 5 and 6 are perspective views of third and fourth embodiments respectively.

Referring now to FIG. 5 there is shown a dental measuring apparatus 50 comprising a table 11 with a datum point 19 and scale 20 marked thereon as with the previously described embodiments. In this case the pillar 12 has a telescopic part 51 thereon which is resiliently biased upwardly relative to the pillar 12 by means of an internal compression spring (not shown). Attached to the telescopic part 51 is a support arm 52 on which the probe 13 is mounted so as to be in axial alignment with the datum point 19. By pressing downwardly on the support arm 52 the telescopic part 51 moves relative to the pillar 12 so that the probe 13 moves towards the datum point 19. A scale 53 on the pillar 12 indicates the distance between the probe 13 and the datum point 19.

Figure 6:
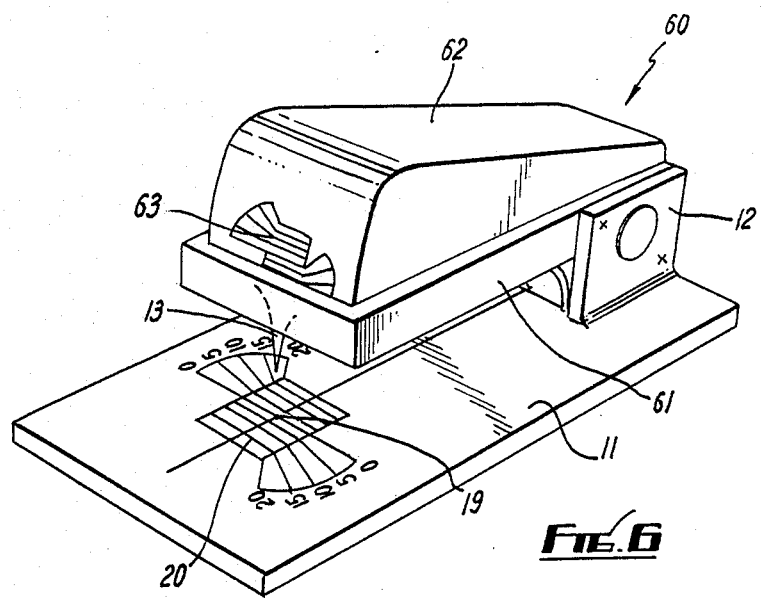

Referring now to FIG. 6 there is shown a dental measuring apparatus 60 comprising a table 11 with a datum point 19 and scale 20 marked thereon. A bracket 12 has a fixed frame 61 mounted thereon and a pivotally mounted support arm 62. The probe 13 is secured to the support arm 62 and a scale 63 is provided on the front of the support arm 62. By pressing down on the support arm 62, the probe 13 is moved towards the datum point 19 and the scale 63 moves relative to the frame 61 so as to indicate the distance of the probe 13 from the datum point 19. The support arm 62 is resiliently biassed upwardly by spring means (not shown).

In practice the apparatus 10, 40, 50, 60 may be used at several stages of the manufacture of dentures, and enables quantitative information to be passed between the technician and the dentist. For example, the afore-mentioned measurements of vertical and horizontal distance of the incisal tip 35 from the datum 34 can be measured on the bite blocks produced by the technician in the laboratory and these measurements can be quoted to the dentist. When the dentist performs the bite registration step, he may decide that for better bite registration, one or more of the dimensions should be altered, and by use of the apparatus 10, 40, 50, 60, he can tell the technician by how much. The technician when setting up the teeth in wax can again use the instrument 10, 40, 50, 60 to ensure that the set-up dentures conform to the original or revised measurements. Again at the try-in, and any re-try stages the dentist can specify quantitatively, using the apparatus 10, 40, 50, 60, any changes to the measured dimensions and the technician can check that the dentures conform to the required dimensions. By this means an accurate positioning of the teeth and bite registration of the dentures can more readily be obtained than was possible using the previous known "trial and error" technique.

As a further embodiment of the invention the table 11 may comprise a heated plate. When producing the bite blocks the technician has previously repeatedly heated and smoothed the bite blocks until they are of the desired height. This is a skilful and time consuming operation. However, with the apparatus of the present invention the model may be placed on the heated table 11 and a zero reading on the apparatus 10, 40, 50, 60 set. The wax may then be added to the model, the apparatus 10, 40, 50, 60 set to the required height dimension and the bite block then lowered towards the hot plate until the correct height dimension is reached. By this means the correct bite block dimension is achieved in a single, simple operation instead of in a time consuming trial and error heat, smooth, check, reheat smooth check process.

The apparatus 10, 40, 50, 60 is particularly useful in the case of the manufacture of replacement dentures. In this case the original dentures can be measured, the dentist can assess whether any alterations to the measured dimensions are required and inform the technician of the measurements to which the new dentures should conform and the technician can produce the new dentures to the required dimensions.

I claim:

1. A hand held operable dental measuring apparatus for taking measurements relative to a reference point on a denture, said apparatus comprising a base plate providing a support surface for said denture, a datum point on said surface, a first scale for indicating distances from said datum point along a path in the plane of said surface, a support means fixed to said plate and projecting upwardly therefrom to one side of said support surface clear of said datum point and said path, a probe having an axis and having a tip thereto, said probe being mounted on said support surface clear of said datum point and said path, a probe having an axis and having a tip thereto, said probe being mounted on said support means above said support surface with said tip aligned with said datum point, said probe being manually movable axially of itself to move said tip towards and away from said datum point, means for restraining movement of said probe transversely to the said axis thereof;

a second scale for indicating the height of said tip above said datum point, whereby by locating the denture on said support surface on top of said datum point and said path and manually moving the probe tip into contact with the said reference point on the denture, the height of the denture at said reference point on the denture, and the spacing of said reference point from a periphery of said denture can be determined respectively from the two scales.

2. A hand held, hand operable dental measuring apparatus for taking measurements relative to a reference point on a denture, said apparatus comprising a base plate providing a support surface for said denture, a datum point marked on said surface, a first scale marked along a path aligned with said datum point on said surfaces for indicating distances from said datum point, a support means fixed to said plate and projecting upwardly therefrom to one side of said support surface clear of said datum point and said first scale, a probe having an axis and having a tip thereto said probe being mounted on said support means above said support surface with said tip vertically aligned with said datum point, said probe being manually movable axially of itself to move said tip vertically towards and away from said datum point, means for restraining movement of said probe transversely to the said axis thereof;

a second scale alongside the said axis of said probe for indicating the height of said tip above said datum point, whereby locating the denture on said support surface on top of said datum point and said first scale and manually moving the probe tip into contact with the said reference point on the denture, the height of the denture at said reference point on the denture, and the spacing of said reference point from a periphery of said denture can be determined respectively from the two scales.

3. A dental measuring apparatus according to claim 2 comprising spring means for resiliently biassing said prove in a direction away from said datum point.

4. A dental measuring apparatus according to claim 2 comprising locking means adapted to releasably secure said probe in any position of adjustment relative to said plate.

5. A dental measuring apparatus according to claim 2 comprising a third scale on said plate adapted to indicate distances on said surface from said datum point in a direction perpendicular to said path.

6. A dental measuring apparatus according to claim 2 wherein said support means comprised a pillar.

7. A dental measuring apparatus according to claim 6, comprising a barrel mounted on said pillar, said barrel having an axial bore in which said probe is slidingly received.

8. A dental measuring apparatus according to claim 7, comprising a cap, wherein said probe has an upper end which is secured in said cap and said cap has an axial bore in which said barrel is slidingly received, and wherein a compression spring is located in said bore of said cap.

9. A dental measuring apparatus according to claim 7 wherein said first scale is marked on said barrel.

10. A dental measuring apparatus according to claim 2 wherein said plate comprises a heated plate.

* * * * *